United States Patent

Ennis, III et al.

[19]

[11] Patent Number: 4,981,472
[45] Date of Patent: Jan. 1, 1991

[54] CANNULA ASSEMBLY FOR SYRINGE

[75] Inventors: James F. Ennis, III, Preston, Conn.; Mark Anderson, R.R. 2, Elmwood, Wis. 54740

[73] Assignee: Mark Anderson, Elmwood, Wis.

[21] Appl. No.: 439,180

[22] Filed: Nov. 20, 1989

[51] Int. Cl.$^5$ .............................................. A61M 5/00
[52] U.S. Cl. ...................... 604/117; 604/239
[58] Field of Search .................. 604/54, 73, 117, 192, 604/263, 278, 239, 197, 198

[56] References Cited

U.S. PATENT DOCUMENTS

| | | | |
|---|---|---|---|
| 3,406,687 | 10/1968 | Moyer | 604/117 |
| 3,434,473 | 3/1969 | Smith | 604/117 |
| 4,453,935 | 6/1984 | Newton | 604/197 |
| 4,737,150 | 4/1988 | Baeumle et al. | 604/198 |
| 4,747,837 | 5/1988 | Hauck | 604/198 |
| 4,850,970 | 7/1989 | Sutherland | 604/117 |
| 4,883,461 | 11/1989 | Sawyer | 604/198 |

Primary Examiner—Stephen C. Pellegrino
Assistant Examiner—Michael Rafa
Attorney, Agent, or Firm—Edward H. Loveman

[57] ABSTRACT

This cannula assembly for injecting medicinal fluid into an animal's teat has a first tapered cannula formed with a circumferential bead at its wider end. A flexible jacket encloses the cannula and has another bead detachably engaging the bead on the cannula. A tapered second cannula extends forwardly from the jacket. This cannula is shorter than the first cannula. A flexible cap has an internal bead which detachably engages a corresponding bead at the sider end of the second cannula. This assembly provides the user with a choice of cannulas of two different sizes in treating a teat. In another form of the invention, a second flexible jacket has a bead which detachably engages a bead on the second cannula. A third cannula extends forwardly from the second jacket. The flexible cap detachably engages a bead on the third cannula, so that the user has a choice of cannulas of three different lengths in treating a teat.

16 Claims, 2 Drawing Sheets

CANNULA ASSEMBLY FOR SYRINGE

BACKGROUND OF THE INVENTION

1. Field of the Invention

This invention relates to the art of syringes used for medical purposes such as treatment of animals for mastitis; and more particularly the invention concerns a novel cannula assembly for a syringe the assembly comprising a plurality of units of different lengths which can be used selectively in administering a mastitis treatment.

2. Description of the Prior Art

It is frequently necessary for a veterinarian or herdsman to treat with medicaments infected teats of animals such as cows, sheep, goats and other animals which suckle their young. Heretofore there has generally been used a syringe having a long tapered cannula of standard size, about an inch or more in length, and about one-eighth of an inch wide at its open free end. In use the cannula is inserted for its full length into the teat of an animal such as a cow or mare, to be treated for mastitis or other infection. However it has been found that a cannula of this length frequently disturbs the natural mucus membrane in the teat and thereby allows the mastitis bacterial to spread its infection. In addition, since the medication is ejected from the cannula a substantial distance from the entry into the teat (one inch or more) the entire teat canal cannot be treated.

SUMMARY OF THE INVENTION

It is therefore a principal object of the present invention to provide a veterinarian, herdsman or other user of a medicinal syringe with a cannula assembly having cannulas of different lengths readily available, so that the user can select one or more cannulas of different lengths in an easy and convenient manner. According to the invention, the long cannula of a syringe is inserted into an adapter in the form of a tubular sleeve or jacket which is detachably mounted on the long cannula. The free end of the jacket is shaped to define a short cannula ranging in axial length from three-eighths to one half inch. On the free end of this jacket is a detachably engaged closed cap. The long cannula and jacket have axially aligned axial bores or passages so that the medicinal fluid can pass freely from the reservoir of the syringe to the open end of the short cannula when the cap is removed. If the user requires a longer cannula the adapter jacket and cap may be removed, leaving only the longer cannula for applying medicinal fluid to the affected teat.

These and other objects and many of the attendant advantages of this invention will be readily appreciated as the same becomes better understood by reference to the following detailed description when considered in connection with the accompanying drawings in which:

BRIEF DESCRIPTION OF THE DRAWINGS

FIG. 5 is an exploded perspective view of parts of the cannula assembly;

DESCRIPTION OF THE PREFERRED EMBODIMENTS

Figure 1:
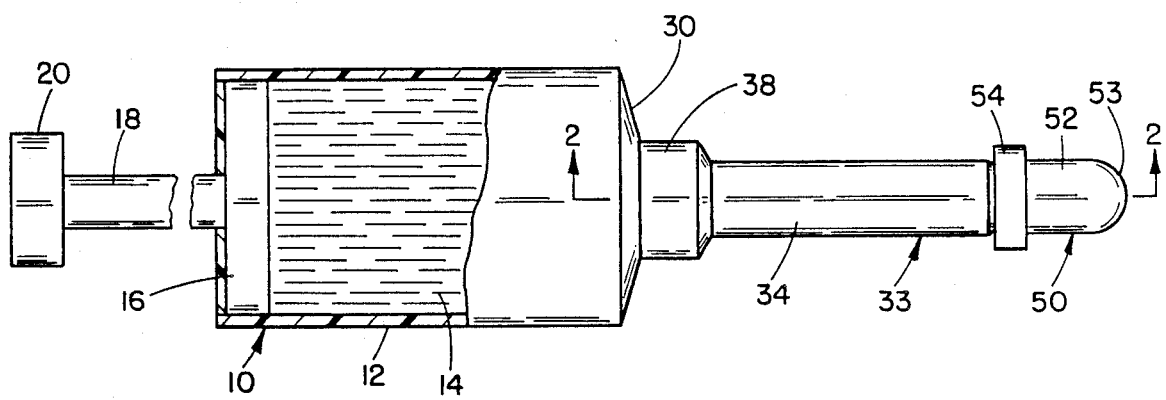
FIG. 1 is a side elevational view of a cannula assembly embodying the invention shown with an associated syringe, parts of which are broken away.

Referring now the drawings wherein like reference characters designate corresponding parts throughout, there is illustrated in FIGS. 1-5, a syringe generally designated as a reference numeral 10 of conventional type. The syringe 10 has a cylindrical body 12 which serves as a reservoir or container of medicinal fluid 14. Inserted in an open left end of the body 12 is a piston head 16 to which is connected a shaft 18 terminating in a knob handle 20 for driving the fluid 14 to the right out of a cannula 22.

Figure 2:
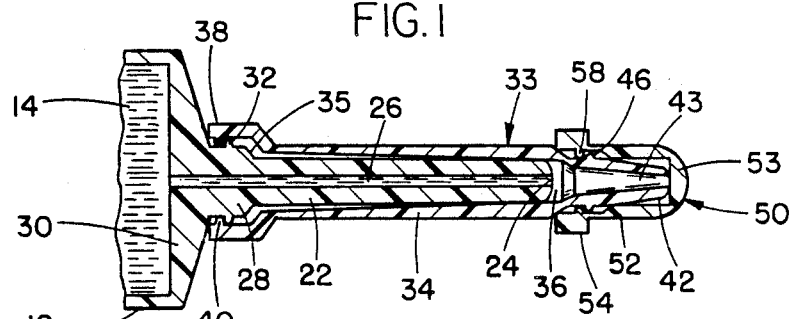
FIG. 2 is a fragmentary longitudinal, axial sectional view taken along line 2—2 of FIG. 1.

The cannula 22 is an elongated tubular member generally frustoconical in shape tapering to a small open end 24 (FIG. 2). In the cannula 22 is an axial passage 26 communicating with the interior of the syringe body 12. The cannula 22 has an enlarged cylindrical section 28 at its base integral with an annular end 30 of the syringe body 12. On the section 28 is formed an integral bead or ridge 32 encircling the section 28. Between the cannula 22 and section 28 is tapered shoulder 35 which serves to seal a teat when fluid 14 is being injected.

Now according to the invention, the cannula 22 is axially inserted into an adapter-33 having the form of flexible cylindrical sleeve or jacket 34 which has an axial bore or passage 36 for receiving the cannula 22. At the open base end of the jacket 34 is an enlarged tubular section 38 formed with an internal circumferential bead or ridge 40 which engages rearwardly of the bead 32. The jacket 34 is flexible so that it can be snapped off section 28 to expose the cannula 22. At the forward end of the adapter 33 is formed a short, tapered cannula 42 having a passage 43 communicating with the bore or passage 36, and with the passage 26. At its base end the cannula 42 is formed with a tapered shoulder 44. Just forwardly of the shoulder 44 is a circumferential bead or ridge 46. The short cannula 42 is open at a forward end 47.

Figure 3:
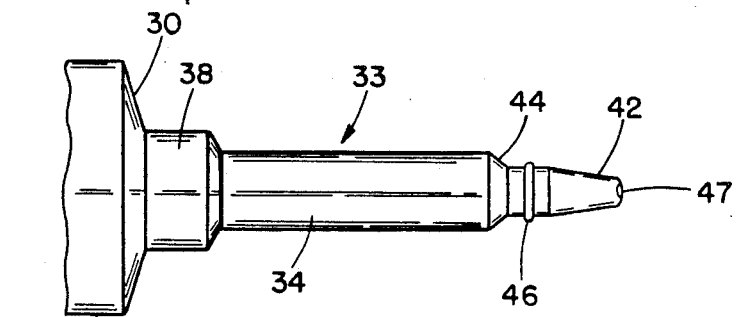
FIG. 3 is a side elevational view of the cannula assembly with short cannula cap removed exposing the shorter cannula.
Figure 4:
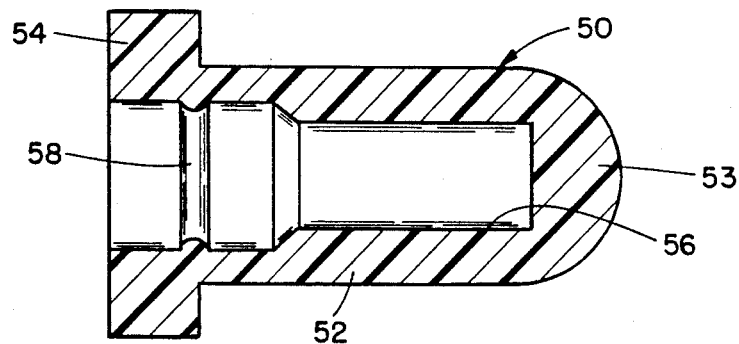
FIG. 4 is an enlarged axial sectional view of the short cannula cap per se.
Figure 6:
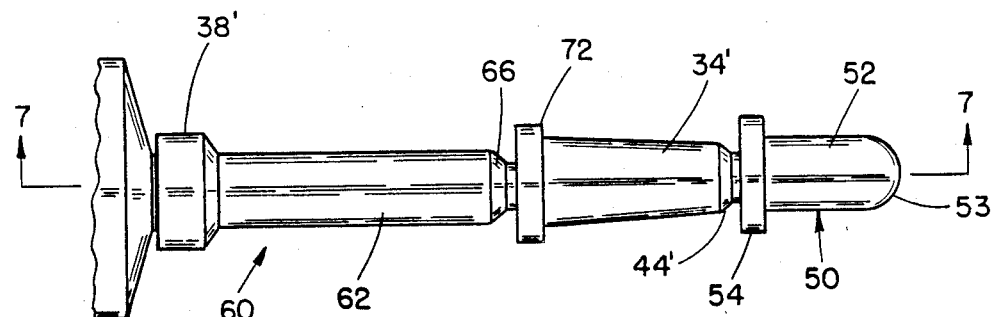
FIG. 6 is a side elevational view of another cannula assembly embodying a modification of the invention, wherein the assembly has two adapter jackets and three cannulas of short, intermediate and long lengths closed by an end cap.

Detachably engaged on the short cannula 42 is a flexible short cannula cap 50 which has a cylindrical body 52; see FIGS. 1, 2 and 4. The body 52 has a closed front end wall 53. At its rear open end, the body 52 has an integral annular flange 54 which serves as a finger grip. Inside the body 52 is a bore 56 formed with a circumferential radially extending bead 58 which detachably engages rearwardly of the bead 46 as shown in FIG. 2. When the flexible short cannula cap 50 is removed from the short cannula 42, the short cannula is exposed as shown in FIG. 3. When the flexible adapter jacket 34 carrying the cap 50 is snapped off the cannula section 28, the longer cannula 22 is exposed. By this arrangement a user can employ either cannula 22 or cannula 42 selectively depending on whether a longer or shorter cannula is required for a particular medicinal treatment. When the flexible adapter jacket 34 is in place the medicinal fluid 14 readily passes through axially aligned passages 26, 36 and 44 to discharge the fluid. Shoulder 44 serves as a stop member limiting insertion of the short cannula 42 into a teat being treated and also serves as a sealing member to prevent leakage of fluid while it is being inserted under pressure out of cannula 42.

The cannula 22 and adapter 33 comprising jacket 34 and cannula 42 constitute a cannula assembly which for the first time makes available to a user different lengths of cannulas in a convenient, compact, sterile and inexpensive way.

It should be understood that it may be necessary in some applications to have a cannula assembly having three cannulas of long, intermediate and short lengths respectively. The principles of the invention can be applied to constructing such a three-cannula assembly as shown in FIGS. 6, 7, 8 and 9 to which reference is now made.

Figure 7:
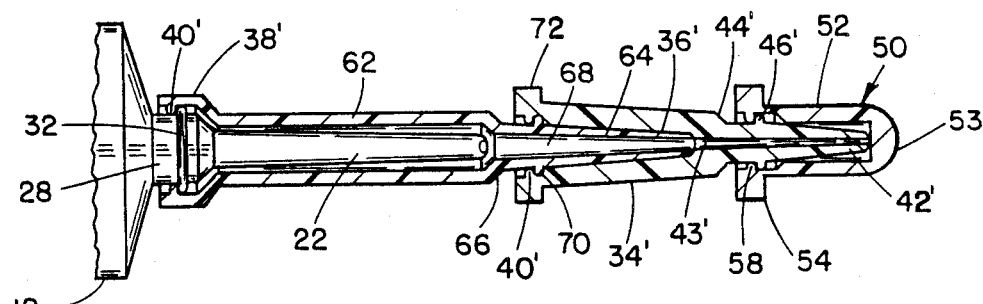
FIG. 7 is a long longitudinal axial sectional view taken along line 7—7 of FIG. 6.

The cannula assembly 60 shown in FIGS. 6–9 has cannula 22 integral with the syringe body 12 arranged and constructed as described above, with the enlarged base section 28 on which is the bead 32. The cannula 22 as best shown in FIG. 7 is inserted into a flexible tubular sleeve or jacket 62 having an enlarged end section 38' formed with an internal bead 40' which engages rearwardly of the bead 32 to hold the flexible jacket removable on the cannula 22. The jacket 62 has an axial extension which is shaped to define a second tapered cannula: 64 having an axial length shorter than that of the cannula 22. A tapered shoulder 66 at the base end of the cannula 64 limits insertion into a teat and seals the teat from leakage of medicinal fluid during injection of fluid under pressure. The cannula 64 has an axial passage 68 communicating with the passage in the cannula 22. A circumferential bead 70 is formed on the cannula 64 just forwardly of the shoulder 66.

Figure 9:
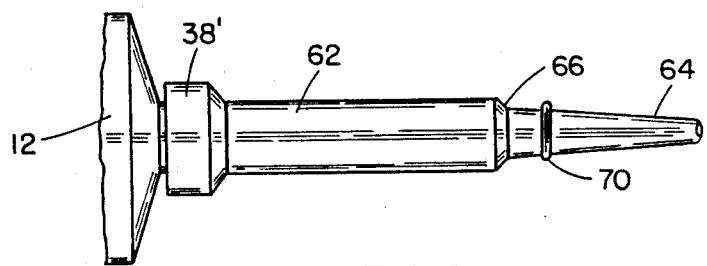
FIG. 9 is a side elevational view of the cannula assembly of FIGS. 6–8 with the forward jacket and cap removed exposing the cannula of intermediate length.
Figure 8:
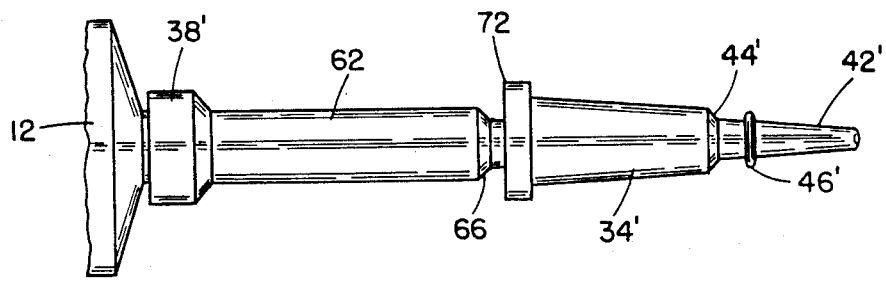
FIG. 8 is a side elevational view of the cannula assembly of FIGS. 6 and 7, with end cap removed exposing the shortest cannula.

A second flexible tubular sleeve or jacket 34' is detachably mounted on the cannula 64. The jacket 34' like the jacket 34 is formed with a short tapered cannula 42' at a forward end. The jacket 34' has an axial passage 36' which receives the cannula 64. The jacket 34' has an annular flange 72 at its open left end. Inside the open end of the flexible jacket 34' is a circumferential bead 40' which engages forwardly of the bead 70. On the cannula 42' just forwardly of a tapered shoulder 44' is a circumferential bead 46'. The flexible cap is the same as shown in FIGS. 1, 2, 4 and 5 engages on the cannula 42' and closes passage 43'. The bead 58 of the cap 50 engages behind the bead 46'. Since the cap 50 is flexible it can be snapped of to expose the shortest cannula 42' as shown in FIG. 8. Similarly, the jacket 34' can be snapped off the cannula 64 along with the cap 50 to expose the intermediate size cannula 64 as shown in FIG. 9. The jacket 62 can be snapped off the cannula 22 along with the jacket 34' and the cap 50 to expose the longest cannula 22. By this arrangement the user has the choice available for selecting a longer, intermediate or shorter cannula for injecting fluid into a teat under treatment. In practice the longest cannula 22 may be at least one inch in length, the intermediate cannula 64 may be about three quarters of an inch in length, and the shortest cannula 42' may be no longer than one half of an inch in length.

All of the syringes and cannulas described are recommended for one-time use to be discarded after use. They can be made economically by mass production machinery at very low cost. They meet a long felt need in the field by making it possible for a user to select the length of cannula needed at the time of injection. Removal of the various flexible jackets and caps requires no tools and no special skills. The caps and cannulas are constructed so as to be leak-proof prior to use and effective during use.

It should be understood that the foregoing relates only to a preferred embodiment of the invention which has been by way of example only, and that it is intended to cover all changes and modifications of the examples of the invention herein chosen for the purpose of the disclosure, which do not constitute departures from the spirit and scope of the invention.

What is claimed is:

1. A cannula assembly for a syringe adapted for discharging medicinal fluid into a teat of an animal being treated, comprising:
   a first cannula having an elongated body of predetermined axial length terminating in a first free open end for discharging said fluid therefrom;
   a tubular jacket enclosing said cannula in axial alignment therewith;
   first means on said cannula and said jacket for detachably engaging together said cannula and said jacket;
   a second cannula integral with said jacket and extending axially forward of said open end of said first cannula in axial alignment therewith for receiving said fluid from said first cannula, said second cannula having an elongated body substantially different in axial length than that of said first cannula and having a second free open end for discharging said fluid therefrom;
   a tubular cap having opposite closed and open ends, said cap enclosing said second cannula when said second cannula is axially inserted into said cap through said open end of said cap; and
   second means on said second cannula and said cap for detachably engaging together said second cannula and said cap;
   whereby a user can select said second cannula for discharging said fluid by detaching said cap from said second cannula, and whereby said user can select said first cannula for discharging said fluid by detaching said jacket from said first cannula.

2. A cannula assembly as claimed in claim 1, wherein each of said first and second cannulas is tapered to a narrow end to facilitate inserting each of said cannulas into a teat of an animal being treated.

3. A cannula assembly as claimed in claim 2, wherein said first cannula has a shoulder at the other end of said first cannula to serve as a stop member and sealing means at the teat of an animal being treated.

4. A cannula assembly as claimed in claim 3, wherein said second cannula has another shoulder at the other end of said second cannula to serve as a stop member and sealing means at the teat of an animal being treated.

5. A cannula as claimed in claim 4, wherein said jacket is formed of flexible material, and wherein said first means comprises radially extending circumferential beads on said first cannula and said jacket, the flexibility of said jacket enabling said jacket to be snapped on said first cannula to engage said beads, and enabling said jacket to be snapped off said first cannula to disengage said beads and permit removal of said jacket from said first cannula.

6. A cannula as claimed in claim 5, wherein said cap is formed of flexible material, and wherein said second means comprises radially extending circumferential other beads on said second cannula and said jacket, the flexibility of said cap enabling said cap to be snapped on said second cannula to engage other said beads, and enabling said cap to be snapped off said second cannula to disengage said beads and permit removal of said cap from said second cannula.

7. A cannula assembly for a syringe adapted for discharging medicinal fluid into a teat of an animal being treated comprising:
   a first cannula having an elongated first body of predetermined axial length terminating in a first free open end for discharging said fluid therefrom,
   a first tubular jacket enclosing said cannula in axial alignment therewith;
   first means on said cannula and said jacket for detachably engaging together said cannula and said jacket;
   a second cannula integral with said jacket and extending axially forward of said open end of said first cannula in axial alignment therewith for receiving said fluid from said first cannula, said second cannula having an elongated body shorter in axial length than that of said first cannula and having a second free open end for discharging said fluid therefrom;
   a second tubular jacket enclosing said second cannula in axial alignment therewith;
   second means on said second cannula and said second jacket for detachably engaging together said second cannula and second jacket;
   a third cannula integral with said second jacket and extending axially forward of said open end of said second cannula in axial alignment therewith for receiving said fluid from said second cannula, said third cannula having an elongated third body shorter in axial length that of said second cannula and having a third free open end for discharging said fluid therefrom;
   a tubular cap having opposite closed and open ends, said cap enclosing said third cannula when waid third cannula is axially inserted into said cap through said open end of said cap; and
   third means on said third cannula and said cap for detachably engaging together said third cannula and said cap;
   whereby a user can select said third cannula for discharging said fluid by detaching said cap from said third cannula, whereby said user can select said second cannula for discharging said fluid by detaching said second jacket from said second cannula, and whereby said user can select said first cannula for discharging said fluid by detaching said first jacket from said first cannula.

8. A cannula assembly as claimed in claim 7, wherein each of said first, second and third cannulas is tapered to a narrow end to facilitate inserting selectively each of said first, second and third cannula bodies respectively into a teat of an animal being treated.

9. A cannula assembly as claimed in claim 8, wherein each of said first, second and third cannulas has a shoulder at the other end of each cannula to serve as a stop member and sealing means at the teat of an animal being treated.

10. A cannula assembly as claimed in claim 9, wherein said first and second jackets and said cap are all formed of flexible material, and wherein said first, second and third means comprises three pairs of radially extending circumferential beads respectively formed on said first cannula and said first jacket, on said second cannula and said second jacket, and on said third cannula and said cap, the flexibility cap enabling said cap to be snapped off said third cannula; the flexibility of said second jacket enabling the same to be snapped off said second cannula, and the flexibility of said first jacket enabling the same to be snapped off said first cannula, to disengage said beads selectively and permit application of a selected cannula to a teat being treated.

11. A cannular assembly as claimed in claim 1, wherein said elongated body of said second cannula is shorter in length then that of said first cannula.

12. A cannula assembly for a syringe adapted for discharging medicinal fluid into a teat of an animal being treated, comprising:
   a first cannula having an elongated body of predetermined axial length terminating in a first free open end for discharging said fluid therefrom;
   a tubular jacket enclosing said cannula in axial alignment therewith;
   first means on said cannula and said jacket for detachably engaging together said cannula and said jacket;
   a second cannula integral with said jacket and extending axially forward of said open end of said first cannula in axial alignment therewith for receiving said fluid from said first cannula, said second cannula having an elongated body substantially different in axial length than that of said first cannula and having a second free open end for discharging said fluid therefrom;
   closure means on said second cannula for closing said free end of said second cannula, whereby a user can select said second cannula for discharging said fluid by removing said closure means from said second cannula, and whereby said user can select said first cannula for discharging said fluid by detaching said jacket from said first cannula.

13. A cannula assembly as claimed in claim 12 wherein said closure means comprises a tubular cap having opposite closed and open ends, said cap enclosing said second cannula when said second cannula is axially inserted into said cap through said open end of said cap.

14. A cannula assembly as claimed in claim 13 further including second means on said second cannula and said cap for detachably engaging together said second cannula and said cap.

15. A cannula assembly as claimed in claim 12 wherein said annular body of said second cannula is shorter in length then that of said first cannula.

16. A cannula assembly as claimed in claim 12 wherein each of said first and second cannulas is tapered to a narrow end to facilitate inserting each of said cannulas into said teat of said animal being treated.

* * * * *

REEXAMINATION CERTIFICATE (1934th)
United States Patent [19]
Ennis, III et al.

[11] B1 4,981,472
[45] Certificate Issued  Feb. 23, 1993

[54] CANNULA ASSEMBLY FOR SYRINGE

[75] Inventors: James F. Ennis, III, Preston, Conn.;
Mark Anderson, R.R. 2, Elmwood, Wis. 54740

[73] Assignee: Mark Anderson, Elmwood, Wis.

Reexamination Request:
No. 90/002,385, Jul. 9, 1991

Reexamination Certificate for:
Patent No.: 4,981,472
Issued: Jan. 1, 1991
Appl. No.: 439,180
Filed: Nov. 20, 1989

[51] Int. Cl.⁵ .............................................. A61M 5/00
[52] U.S. Cl. ..................................... 604/117; 604/239
[58] Field of Search .................. 604/54, 73, 117, 792, 604/263, 278, 239, 197, 198

[56] References Cited
U.S. PATENT DOCUMENTS

| | | | |
|---|---|---|---|
| 2,908,609 | 5/1956 | Aterno et al. | |
| 3,292,624 | 12/1966 | Gabriel | 128/221 |
| 4,059,112 | 11/1977 | Tischlinger | 128/272.3 |
| 4,850,970 | 7/1989 | Sutherland | 604/117 |

*Primary Examiner*—Stephen C. Pellegrino

[57] ABSTRACT

This cannula assembly for injecting medicinal fluid into an animal's teat has a first tapered cannula formed with a circumferential bead at its wider end. A flexible jacket encloses the cannula and has another bead detachably engaging the bead on the cannula. A tapered second cannula extends forwardly from the jacket. This cannula is shorter than the first cannula. A flexible cap has an internal bead which detachably engages a corresponding bead at the sider end of the second cannula. This assembly provides the user with a choice of cannulas of two different sizes in treating a teat. In another form of the invention, a second flexible jacket has a bead which detachably engages a bead on the second cannula. A third cannula extends forwardly from the second jacket. The flexible cap detachably engages a bead on the third cannula, so that the user has a choice of cannulas of three different lengths in treating a teat.

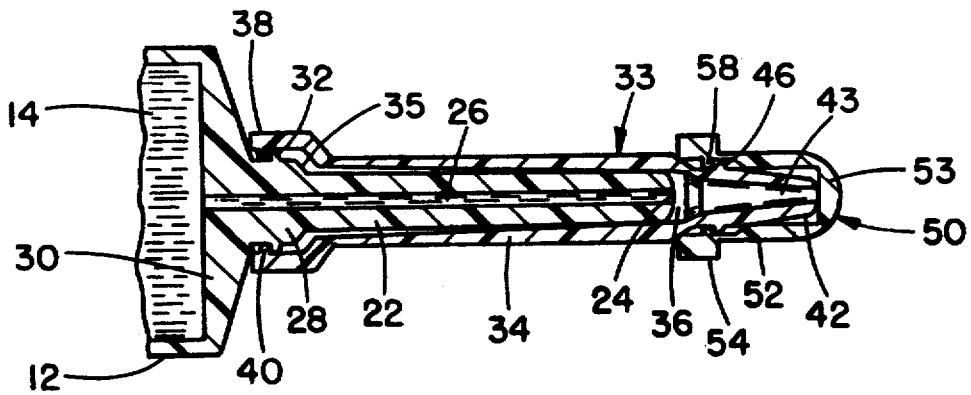

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 29–54:

The cannula 22 is an elongated tubular member generally frustoconical in shape tapering to a small open blunt end 24 (FIG. 2). In the cannula 22 is an axial passage 26 communicating with the interior of the syringe body 12. The cannula 22 has an enlarged cylindrical section 28 at its base integral with an annular end 30 of the syringe body 12. On the section 28 is formed an integral bead or ridge 32 encircling the section 28. Between the cannula 22 and section 28 is tapered shoulder 35 which serves to seal a teat when fluid 14 is being injected.

Now according to the invention, the cannula 22 is axially inserted into an adaptor 33 having the form of flexible cylindrical sleeve or jacket 34 which has an axial bore or passage 36 for receiving the cannula 22. At the open base end of the jacket 34 is an enlarged tubular section 38 formed with an internal circumferential bead or ridge 40 which engages rearwardly of the bead 32. The jacket 34 is flexible so that it can be snapped off section 28 to expose the cannula 22. At the forward end of the adaptor 33 is formed a short, tapered cannula 42 having a passage 43 communicating with the bore or passage 36, and with the passage 26. At its base end the cannula 42 is formed with a tapered shoulder 44. Just forwardly of the shoulder 44 is a circumferential bead or ridge 46. The short cannula 42 is open at a forward *blunt* end 47.

Column 3, lines 1–10:

cannula 42 selectively *and safely inserting each cannula into the central canal of an animal's teat. The blunt ends 24 and 47 of the cannulas prevent the cannulas from piercing the lateral axial wall of the central canal. Cannula 22 or 42 is used* depending on whether a longer or shorter cannula is required for a particular medicinal treatment. When the flexible adaptor jacket 34 is in place the medicinal fluid 14 readily passes through axially aligned passages 26, 36 and 44 to discharge the fluid. Shoulder 44 serves as a stop member limiting insertion of the short cannula 42 into *the central canal of* a teat being treated and also serves as a sealing member to prevent leakage of fluid while it is being inserted under pressure out of cannula 42.

AS A RESULT OF REEXAMINATION, IT HAS BEEN DETERMINED THAT:

The patentability of claims 7–11 is confirmed.

Claims 1 and 12 are determined to be patentable as amended.

Claims 2–6 and 13–16, dependent on an amended claim, are determined to be patentable.

1. A cannula assembly for a syringe adapted for discharging medicinal fluid *different selected distances* into a *central canal of* a teat of an animal being treated, *said canal having an imperforate, axial, lateral wall in said teat*, comprising:

a first cannula having an elongated body of predetermined axial length terminating in a first free open blunt end *for safely entering said central canal without piercing said axial, lateral wall thereof and* for discharging said fluid therefrom *into said canal;* a tubular jacket enclosing said cannula in axial alignment therewith;

first *threadless* means on said cannula and said jacket for *quickly* detachably engaging together said cannula and said jacket;

a second cannula integral with said jacket and extending axially forward of said open *blunt* end of said first cannula in axial alignment therewith for receiving said fluid from said first cannula, said second cannula having an elongated body substantially different in axial length [than] *from* that of said first cannula and having a second free open blunt end *for safely entering said central canal without piercing said axial, lateral wall thereof and* for discharging said fluid therefrom *into said canal;* a tubular cap having opposite closed and open ends, said cap enclosing *said open blunt end* of said second cannula when *said open blunt end of* said second cannula is axially inserted into said cap through said open end of said cap; and second *threadless* means on said second cannula and said cap for *quickly* detachably engaging together said second cannula and said cap;

whereby a user can select said second cannula for discharging said fluid *only into said central canal of said teat without piercing said axial, lateral wall of said canal,* by detaching said cap from said second cannula, and whereby said user can select said first cannula for discharging said fluid *only into said central canal of said teat without piercing said axial, lateral wall of said canal,* by detaching said jacket from said first cannula.

12. A cannula assembly for a syringe adapted for *safely* discharging medicinal fluid *different selected distances* into a *central canal of* a teat of an animal being treated, *said canal having an imperforate, axial, lateral wall in said teat*, comprising:

a first cannula having an elongated body of predetermined axial length terminating in a first free open blunt end *for safely entering said central canal without piercing said axial, lateral wall thereof and* for discharging said fluid therefrom *into said canal;* a tubular jacket enclosing said cannula in axial alignment therewith;

first *threadless* means on said cannula and said jacket for *quickly* detachably engaging together said cannula and said jacket;

a second cannula integral with said jacket and extending axially forward of said open *blunt* end of said first cannula in axial alignment therewith for receiving said fluid from said first cannula, said second cannula having an elongated body substantially different in axial length [than] *from* that of said first cannula and having a second free open end *for safely entering said central canal without piercing said axial, lateral wall thereof and* for discharging said fluid therefrom *into said canal;* a *threadless* closure means on said second cannula for closing said *second* free *open blunt* end of said second cannula, whereby a user can select said second cannula for discharging said fluid by removing said *threadless* closure means from said second cannula, and whereby said user can select said first cannula for discharging said fluid *into said central canal of said teat without piercing said axial, lateral wall of said canal,* by detaching said jacket from said first cannula.

* * * * *

REEXAMINATION CERTIFICATE (3081st)

United States Patent [19]
Ennis, III et al.

[11] B2 4,981,472
[45] Certificate Issued Dec. 24, 1996

[54] CANNULA ASSEMBLY FOR SYRINGE

[75] Inventors: James F. Ennis, III, Preston, Conn.; Mark Anderson, R.R. 2, Elmwood, Wis. 54740

[73] Assignee: Mark Anderson, Elmwood, Wis.

Reexamination Request:
No. 90/003,123, Jul. 9, 1993

Reexamination Certificate for:
Patent No.: 4,981,472
Issued: Jan. 1, 1991
Appl. No.: 439,180
Filed: Nov. 20, 1989

Reexamination Certificate B1 4,981,472 issued Feb. 23, 1993

[51] Int. Cl.$^6$ ............................................. A61M 5/00
[52] U.S. Cl. ................................. 604/117; 604/239
[58] Field of Search ...................... 604/54, 73, 117, 604/192, 263, 238, 239, 197, 198

[56] References Cited

U.S. PATENT DOCUMENTS

| | | | |
|---|---|---|---|
| 2,626,603 | 1/1953 | Gabriel | 128/218 |
| 4,127,126 | 11/1978 | Schunk | 128/234 |
| 4,296,747 | 10/1981 | Ogle | 128/220 |
| 4,405,322 | 9/1983 | Jessup | 604/232 |
| 4,850,970 | 7/1989 | Sutherland | 604/117 |

FOREIGN PATENT DOCUMENTS

WO84/03840 10/1984 United Kingdom.

*Primary Examiner*—Corrine Maglione

[57] ABSTRACT

This cannula assembly for injecting medicinal fluid into an animal's teat has a first tapered cannula formed with a circumferential bead at its wider end. A flexible jacket encloses the cannula and has another bead detachably engaging the bead on the cannula. A tapered second cannula extends forwardly from the jacket. This cannula is shorter than the first cannula. A flexible cap has an internal bead which detachably engages a corresponding bead at the sider end of the second cannula. This assembly provides the user with a choice of cannulas of two different sizes in treating a teat. In another form of the invention, a second flexible jacket has a bead which detachably engages a bead on the second cannula. A third cannula extends forwardly from the second jacket. The flexible cap detachably engages a bead on the third cannula, so that the user has a choice of cannulas of three different lengths in treating a teat.

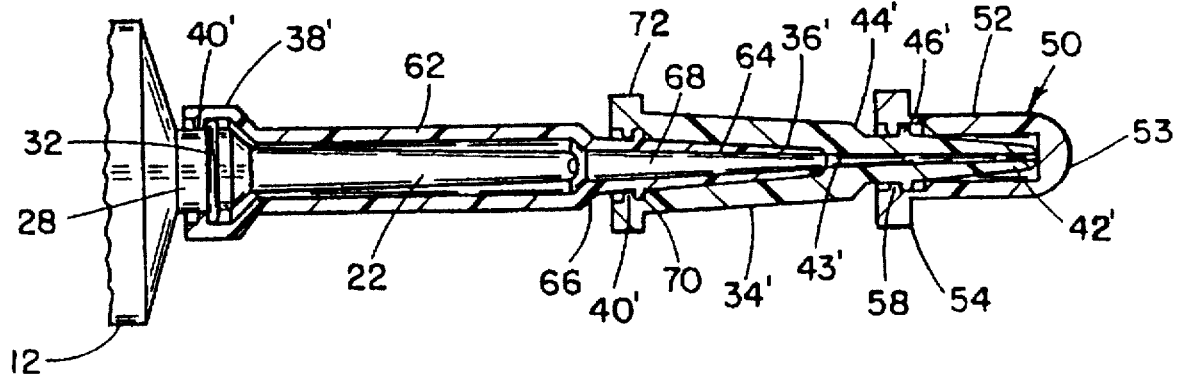

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 7–10 is confirmed.

Claims 1–6 and 11–16 are cancelled.

* * * * *